(12) United States Patent
Borus et al.

(10) Patent No.: US 10,945,801 B2
(45) Date of Patent: Mar. 16, 2021

(54) SOFT TISSUE CUTTING INSTRUMENT AND METHOD OF USE

(71) Applicant: MAKO Surgical Corp., Fort Lauderdale, FL (US)

(72) Inventors: Todd Borus, Vancouver, WA (US); Carinne Cecile Granchi, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 589 days.

(21) Appl. No.: 13/900,484

(22) Filed: May 22, 2013

(65) Prior Publication Data

US 2013/0317344 A1 Nov. 28, 2013

Related U.S. Application Data

(60) Provisional application No. 61/650,273, filed on May 22, 2012.

(51) Int. Cl.
*A61B 19/00* (2006.01)
*A61B 34/00* (2016.01)
(Continued)

(52) U.S. Cl.
CPC .............. *A61B 34/76* (2016.02); *A61B 34/10* (2016.02); *A61B 34/20* (2016.02);
(Continued)

(58) Field of Classification Search
CPC .............. A61B 2019/5236; A61B 5/05; A61B 19/5244; A61B 17/320068;
(Continued)

(56) References Cited

U.S. PATENT DOCUMENTS

| 8,010,180 B2 | 8/2011 | Quaid et al. |
| 2003/0153978 A1 | 8/2003 | Whiteside |

(Continued)

FOREIGN PATENT DOCUMENTS

| CN | 101160104 A | 4/2008 |
| EP | 1 571 581 | 9/2005 |
| WO | WO-2010/151564 | 12/2010 |

OTHER PUBLICATIONS

International Search Report and Written Opinion for International Application No. PCT/US2013/042309, dated Sep. 4, 2013, 18 pages.

*Primary Examiner* — Jeffrey G Hoekstra
*Assistant Examiner* — Katherine M McDonald
(74) *Attorney, Agent, or Firm* — Foley & Lardner LLP

(57) ABSTRACT

A surgical apparatus includes a surgical device and a surgical controller. The surgical device is configured to be manipulated by a user to perform a soft tissue cutting procedure on a patient. The surgical controller is programmed to create a virtual object representing an anatomy of the patient based upon data acquired during a pre-operative scan and associate the virtual object with the anatomy of the patient. The surgical controller is also programmed to identify a plurality of soft tissue attachment points on the virtual object which correspond to a plurality of soft tissue attachment points on the anatomy of the patient. The surgical controller is also programmed to determine the location of the surgical device in relation to the anatomy of the patient and provide real-time visualization on the virtual object of the location of the surgical device in relation to the anatomy of the patient.

32 Claims, 12 Drawing Sheets

(51) Int. Cl.
  *A61B 34/20*  (2016.01)
  *A61B 34/10*  (2016.01)
  *A61B 18/14*  (2006.01)
  *A61B 90/00*  (2016.01)
  *A61B 17/17*  (2006.01)
  *A61B 17/00*  (2006.01)

(52) U.S. Cl.
  CPC ....... *A61B 17/1742* (2013.01); *A61B 18/1402* (2013.01); *A61B 2017/00123* (2013.01); *A61B 2034/105* (2016.02); *A61B 2034/107* (2016.02); *A61B 2034/2055* (2016.02); *A61B 2090/08021* (2016.02); *A61B 2090/374* (2016.02); *A61B 2090/3762* (2016.02)

(58) Field of Classification Search
  CPC ..... A61B 17/1742; A61B 34/20; A61B 34/76; A61B 34/10; A61B 2034/2055; A61B 2034/105; A61B 2034/107; A61B 2090/08021; A61B 2090/374; A61B 2090/3762; A61B 18/1402; A61B 2017/00123
  USPC .................................................. 600/416, 411
  See application file for complete search history.

(56) References Cited

U.S. PATENT DOCUMENTS

| | | |
|---|---|---|
| 2006/0142656 A1 | 6/2006 | Malackowski et al. |
| 2007/0249967 A1 | 10/2007 | Buly et al. |
| 2009/0209884 A1 | 8/2009 | Van Vorhis et al. |
| 2011/0092804 A1 | 4/2011 | Schoenefeld et al. |

SOFT TISSUE CUTTING INSTRUMENT AND METHOD OF USE

CROSS-REFERENCE TO RELATED APPLICATIONS

This application claims the benefit of and priority to U.S. Provisional Application No. 61/650,273, filed May 22, 2012, which is incorporated herein by reference in its entirety.

BACKGROUND

The present application relates generally to a surgical cutting instrument, system, and method of use thereof for orthopedic joint arthroplasty, and more particularly to a surgical instrument, system, and method to assist with soft tissue releases that may be beneficial in joint arthroplasty applications for the hip, knee, and shoulder.

Direct anterior total hip replacement is a surgical approach for total hip replacement which is gaining in popularity. This approach involves accessing the target region at an intramuscular interval between the tensor fascia lata muscle and sartorius, potentially allowing for less soft tissue trauma and earlier patient recovery. A specific challenge related to direct anterior total hip replacement is achieving adequate femoral exposure for placement of the femoral prosthesis. In order to provide appropriate femoral exposure, proper identification of the soft tissue release locations is required, followed by releases of the soft tissues around the proximal femur in a certain sequence. These release locations and sequence may include releasing the medial hip capsule toward the level of the lesser trochanter, releasing the lateral hip capsule from the inner surface of the greater trochanter, and possibly performing a selective release of specific external rotator tendons from the posterior border of the femur. A challenge in the learning curve of direct anterior total hip replacement is properly identifying the release locations and mastering the degree and sequence of releases required. Failure to achieve adequate exposure on the femur for the procedure can make the procedure extremely challenging. Furthermore, visualization during direct anterior total hip replacement can be quite onerous. It can be difficult to determine the location of specific bony landmarks on the proximal femur, which can certainly render the locations of appropriate releases more difficult to determine.

There are other applications that utilize a methodical soft tissue release procedure that may also require proper identification of the soft tissue release locations and a defined release order, such as in knee replacement and ligament balancing, and shoulder arthroplasty and rotator cuff repairs. For example, in a knee procedure, various releases are required for correcting certain varus and valgus deformities.

SUMMARY

According to various embodiments, a beneficial surgical system, and method to provide optimal guidance for identifying soft tissue release locations and performing the necessary tissue releases in hip, knee, and shoulder arthroplasty are provided. One aspect of the invention relates to a surgical apparatus including a surgical device configured to be manipulated by a user to perform a soft tissue cutting procedure on a patient and a surgical controller. The surgical controller is programmed to create a virtual object representative of the anatomy of the patient that is based upon data acquired during a pre-operative scan. The surgical controller is also programmed to associate the virtual object with the anatomy of the patient and to identify a plurality of soft tissue attachment points on the virtual object which correspond to a plurality of soft tissue attachment points on the anatomy of the patient. The surgical controller is also programmed to detect the location of the surgical device in relation to the anatomy of the patient and to provide real-time visualization on the virtual object of the location of the surgical device in relation to the anatomy of the patient.

Another aspect of the invention relates to a method of providing visual guidance for soft tissue releases during a joint arthroplasty procedure. The method includes the steps of providing a surgical device and a surgical controller. The surgical controller is configured: to create a virtual image representing an anatomy of the patient based upon data acquired during a pre-operative scan and to associate the virtual image with the anatomy of the patient. The surgical controller is also programmed to identify a plurality of soft tissue attachment points on the virtual object which correspond to a plurality of soft tissue attachment points on the target anatomy, to detect the location of the surgical device in relation to the target anatomy, and to provide real-time visualization on the virtual object of the location of the surgical device in relation to the target anatomy. The method also includes utilizing the pre-operative scan data to create a virtual image of the target anatomy and associating the patient's anatomy with this virtual image, then identifying on the virtual image the soft tissue attachment points on at least one bone of the target anatomy to provide visualization of the soft tissue release locations. The method also includes providing a tracking system to track movement of the surgical tool in relation to the target anatomy, the surgical tool having a tracking element that is trackable by the tracking system. Finally, the method includes identifying on the virtual image the location of the surgical tool in relation to the target anatomy to assist with the execution of soft tissue releases at and around the joint during arthroplasty.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Figure 1:
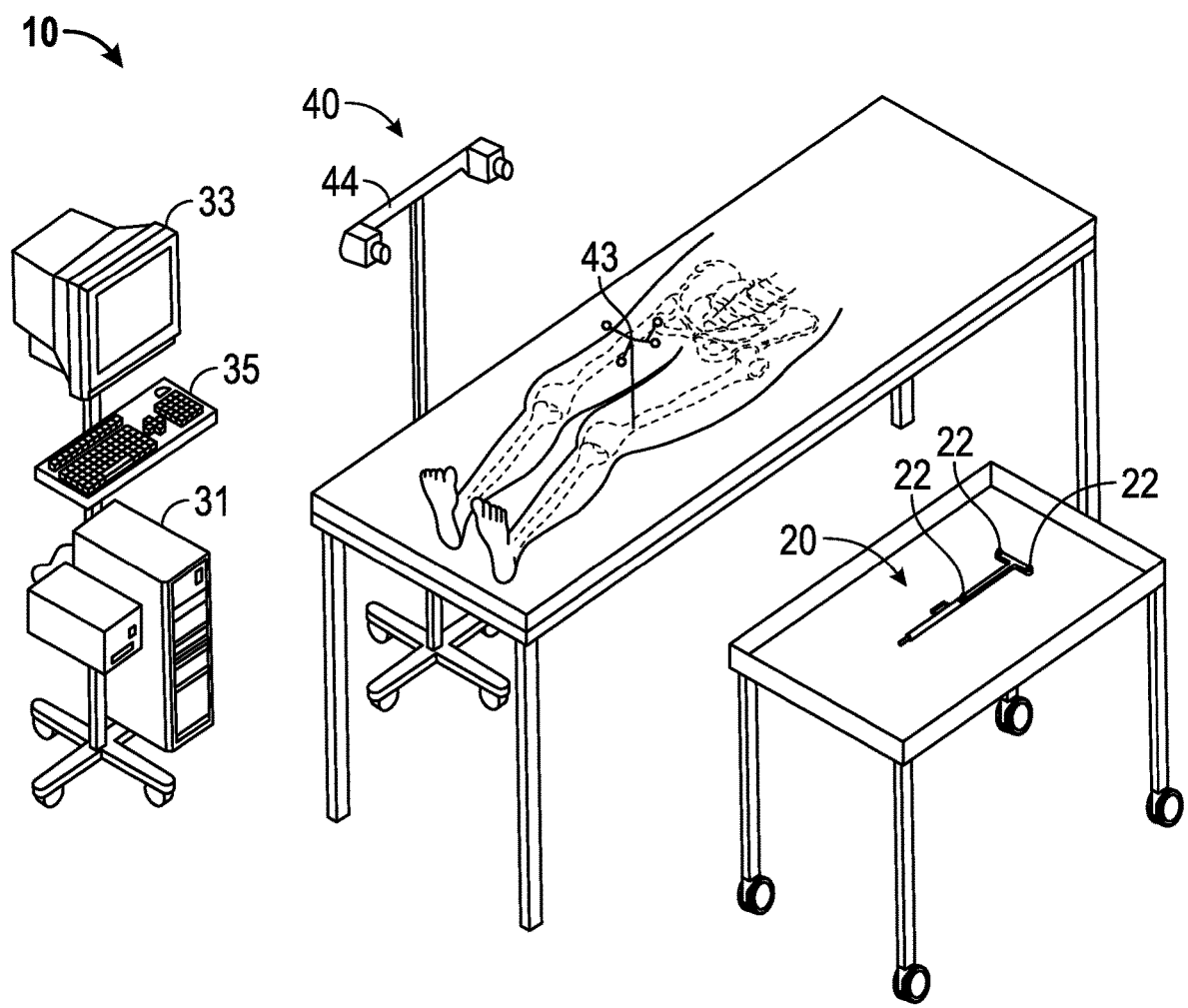
FIG. 1 is a perspective view of a surgical system according to an exemplary embodiment.

Referring to FIG. 1, according to an exemplary embodiment, a soft tissue cutting instrument, shown as cutting device 20 is used in connection with a surgical system 10. As shown, the surgical system 10 includes the cutting device 20, a computing system 30, and a tracking system 40.

Figure 2:
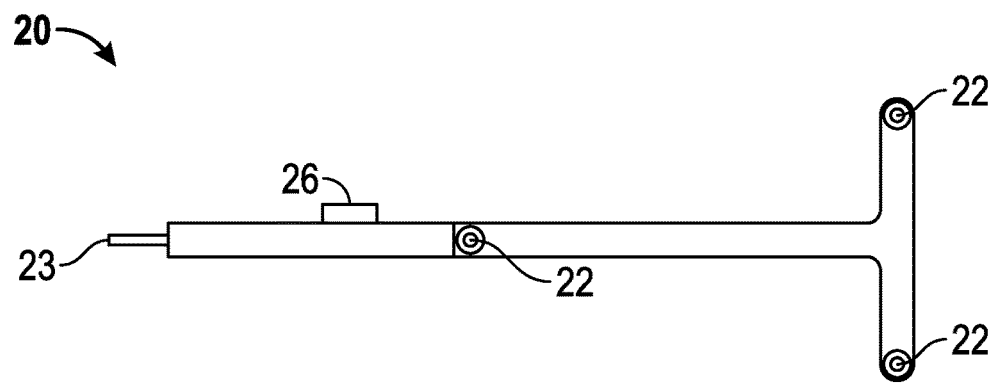
FIG. 2 is a plan view of a cutting instrument according to an exemplary embodiment.
Figure 3:
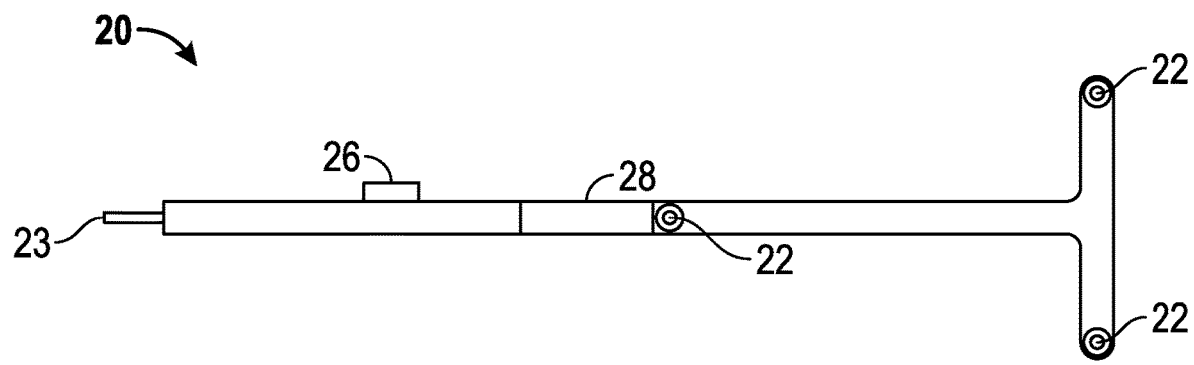
FIG. 3 is a plan view of a cutting instrument according to an exemplary embodiment.

Referring to FIGS. 1-3, in an exemplary embodiment, the cutting device 20 is affixed with tracking elements 22 which reflect infrared light to be recognized by the tracking system 40, which is explained in greater detail below. The tracking elements 22 may be incorporated into the cutting device 20, as shown in FIG. 2, or the tracking elements 22 may be attached as an outrigger, such as a modular attachment 28, to cutting device 20, as shown in FIG. 3. The cutting tip 23 of the cutting device 20 may be a scalpel blade, but in a preferred embodiment is an electrocautery device, ultrasonic cutting tool, or vibratory cutting device which would provide hemostasis. The cutting device 20 may further have an activation device, such as activation button 26, to be manipulated for activation of the cutting device 20.

Figure 4:
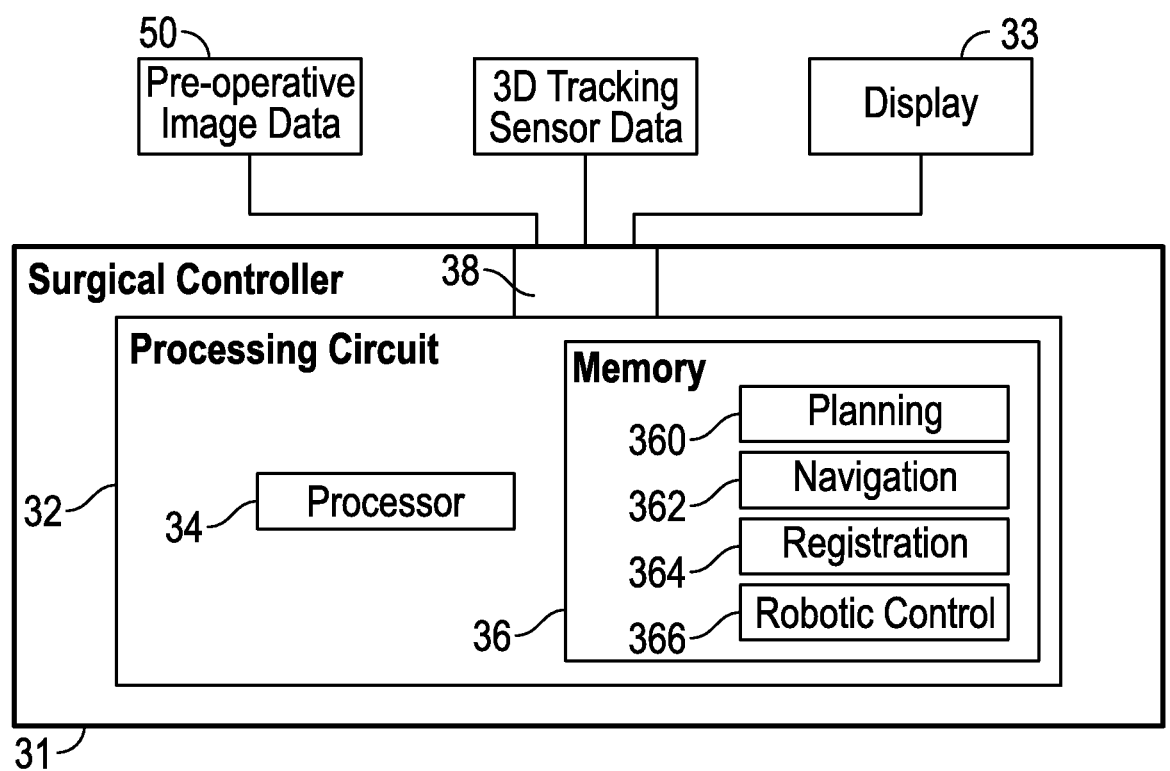
FIG. 4 is a block diagram of a model surgical controller according to an exemplary embodiment.

The computing system 30 includes hardware and software for operation and control of the surgical system 10. According to an exemplary embodiment, the computing system 30 includes a surgical controller 31, a display device 33, and an input device 35. Referring to FIG. 4, in an exemplary embodiment, the surgical controller 31 includes a processing circuit 32 having a processor 34 and memory 36. Processor 34 can be implemented as a general purpose processor, an application specific integrated circuit (ASIC), one or more field programmable gate arrays (FPGAs), a group of processing components, or other suitable electronic processing components. Memory 36 (e.g., memory, memory unit, storage device, etc.) is one or more devices (e.g., RAM, ROM, Flash-memory, hard disk storage, etc.) for storing data and/or computer code for completing or facilitating the various processes described in the present application. Memory 36 may be or include volatile memory or non-volatile memory. Memory 36 may include database components, object code components, script components, or any other type of information structure for supporting the various activities described in the present application. According to an exemplary embodiment, memory 36 is communicably connected to processor 34 and includes computer code for executing one or more processes described herein. The memory 36 may contain a variety of modules, each capable of storing data and/or computer code related to specific types of functions. In one embodiment, memory 36 contains several modules related to surgical procedures, such as a planning module 360, a navigation module 362, a registration module 364, and a robotic control module 366.

Referring still to FIG. 4, the surgical controller 31 further includes a communication interface 38. The communication interface 38 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.).

According to an exemplary embodiment, prior to a surgical procedure, pre-operative image data of any form (e.g., two-dimensional images, a three-dimensional model) 50 is transmitted to the surgical controller 31 via the communication interface 38. The pre-operative image data 50 can then be utilized during the development of a surgical plan, which may include identifying the release locations for a direct anterior total hip replacement. The identification of these release locations will be described in greater detail below. To obtain the pre-operative image data 50, a patient may be scanned using any known imaging technique, such as CT, MRI, or ultrasound. The scan data is then segmented (either by the surgical controller 31 or by another processor) to obtain a three-dimensional representation of a portion of the patient's anatomy, such as the patient's hip. In another embodiment, a three-dimensional representation may be obtained by selecting a three-dimensional model from a database or library of bone models. The selected bone model(s) from the database can then be deformed based on specific patient characteristics to obtain a three-dimensional representation of a portion of the patient's anatomy. For use in a direct anterior total hip replacement, the bone models created by scanned image data and/or the database may also be used to determine and show the location of the soft tissue surrounding the target bones, some of which may need to be released in order to achieve proper exposure of the femur. The three-dimensional representations of the patient's anatomy may be displayed on the display device 33, such as a computer screen or tablet device.

The planning module 360, located in memory 36 of the surgical controller 31, can store the instructions necessary to process the incoming pre-operative image data and to utilize the image data during surgical planning Once the three-dimensional representation of a portion of the patient's anatomy has been created, a surgeon can develop a surgical plan based on the three-dimensional representation. The surgical plan may include the desired soft tissue releases, the desired modifications to bone (e.g., holes, cuts) to be created during the surgical procedure, and may further include the desired placement for any components to be implanted during the surgical procedure.

Prior to utilizing the cutting device 20 during a surgical procedure and implementing the surgical plan, the patient's actual anatomy is registered to the three-dimensional representation of the patient's anatomy. Registration processes involve correlating the coordinate system of the patient's actual anatomy (in physical space) to the coordinate system of the three-dimensional representation of the patient's anatomy (in virtual space). One possible registration technique is point-based registration, as described in U.S. Pat. No. 8,010,180, titled "Haptic Guidance System and Method," granted Aug. 30, 2011, which is incorporated by reference herein in its entirety. Once registered to the virtual representation, the pose of the patient's anatomy can be tracked in real-time during the surgical procedure, as described further below. Tracking the patient's anatomy, as well as the location of cutting device 20, is used to ensure proper implementation of a surgical plan, including performing the proper soft tissue releases as required in direct anterior total hip replacement.

The registration process and the on-going tracking may be carried out by the tracking system 40. The tracking system 40 may be any tracking system that enables the surgical system 10 to continually determine (or track) a pose of the relevant anatomy of the patient and a pose of the cutting device 20. For example, the tracking system 40 may include a non-mechanical tracking system, a mechanical tracking system, or any combination thereof suitable for use in a surgical environment. The non-mechanical tracking system may include an optical (or visual), magnetic, radio, or acoustic tracking system. Such systems typically include a detection device, such as detection device 44 shown in FIG. 1, adapted to locate in predefined coordinate space one or more specially recognizable trackable elements or trackers, such as tracking elements 22 on the cutting device 20. As noted above with respect to tracking elements 22, the trackable elements of a tracking system 40 may be configured to be attached to the object to be tracked (such as cutting device 20) or may be an inherent part of the object to be tracked. The trackable element may include an array of markers having a unique geometric arrangement and a known geometric relationship to the tracked object when the trackable element is attached to the tracked object. Thus, the detection device can recognize a particular tracked object, at least in part, from the geometry of the markers (if unique), an orientation of the axis, and a location of the endpoint within a frame of reference deduced from positions of the markers. The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

In one embodiment, as shown in FIG. 1, the tracking system 40 includes a non-mechanical tracking system. In this embodiment, the non-mechanical tracking system is an optical tracking system that includes a detection device 44 and at least one trackable element or tracker (such as tracking element 22) configured to be disposed on (or incorporated into) a tracked object (such as cutting device 20) and detected by the detection device 44. As shown in FIG. 1, the detection device 44 may include, for example, a stereo camera pair sensitive to infrared radiation and positionable in an operating room where the surgical procedure will be performed. The tracking element 22 is configured to be affixed to the tracked object, such as the cutting device 20, in a secure and stable manner and includes an array of markers having a known geometric relationship to the tracked object. The markers may be active (e.g., light emitting diodes or LEDs) or passive (e.g., reflective spheres, a checkerboard pattern, etc.) and preferably have a unique geometry (e.g., a unique geometric arrangement of the markers) or, in the case of active, wired markers, a unique firing pattern. In operation, the detection device 44 detects positions of the markers, and the unique geometry (or firing pattern) and known geometric relationship to the tracked object enable the surgical system 10 to calculate a pose of the tracked object based on the positions of the markers.

Because the tracking system 40 relies on an ability of the detection device 44 to optically "see" the markers, the detection device 44 and the tracking elements 22 should be positioned so that a clear line of sight between the detection device 44 and the tracking elements 22 is maintained during the surgical procedure. As a safeguard, the surgical system 10 is preferably configured to alert the user if the detection device 44 is unable to detect the tracking elements 22 during the procedure (e.g., when the line of sight between the detection device 44 and one or more of the markers is blocked and/or when reflectivity of the markers is occluded). For example, the surgical system 10 may include an audible (and/or visual) alarm programmed to sound (and/or flash) when a person steps between the markers and the detection device 44, when an object is interposed between the markers and the detection device 44, when a lens of the camera is occluded (e.g., by dust), and/or when reflectivity of the markers is occluded (e.g., by blood, tissue, dust, bone debris, etc.). The surgical system 10 may also include programming to trigger other safety features, such as, for example, an occlusion detection algorithm with a power shutoff feature that disables the cutting device 20 when the detection device 44 loses sight of the tracking elements 22.

The non-mechanical tracking system may include a trackable element (or tracker) for each object the user desires to track.

Figure 5:
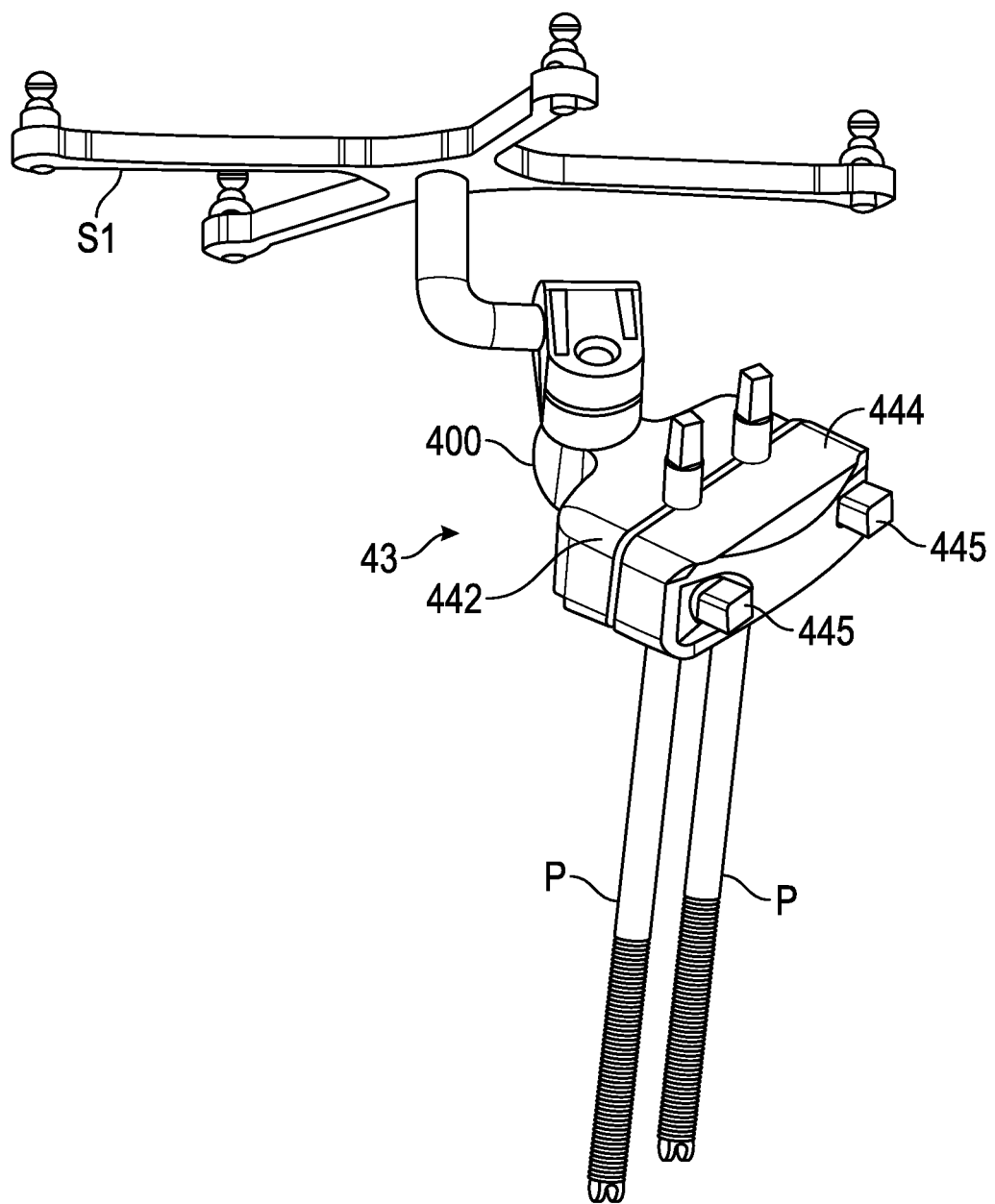
FIG. 5 is a perspective view of an anatomy tracker according to an exemplary embodiment.

As shown in FIG. 1, an anatomy tracker 43 is disposed on a portion of a patient's anatomy (such as a bone) and is adapted to enable the anatomy to be tracked by the detection device 44. The anatomy tracker 43 includes a fixation device for attachment to the anatomy. The fixation device may be, for example, a bone pin, surgical staple, screw, clamp, wearable device, intramedullary rod, or the like. In one embodiment, shown in FIG. 1, an anatomy tracker 43 is configured for use during hip replacement surgery to track a pelvis of a patient. In a knee replacement application, the anatomy tracker may include a first tracker adapted to be disposed on the femur and a second tracker adapted to be disposed on the tibia. As shown in FIG. 5, the tracker 43 includes a fixation device including bone pins P and a unique array S1 of markers (e.g., reflective spheres). The array S1 is affixed to a connection mechanism 400 that is adapted to be removably secured to both of the bone pins P. For example, as shown in FIG. 5, the connection mechanism 400 may include a first portion 442, a second portion 444, and screws 445. To install the tracker 43 on the bone, the user screws the bone pins P into the bone, slides the connection mechanism 400 over the bone pins P, and tightens the screws 445 to draw the first and second portions 442 and 444 together to thereby securely fix the connection mechanism 400 to the bone pins P. Once secured, the connection mechanism 400 imparts additional stability to the bone pins P. Additional trackers, as needed, are identical to the tracker 43 except additional trackers are installed on different points on the anatomy or different bones, and each may have its own uniquely configured array of markers. When installed on the patient, the tracker 43 or trackers enable the detection device 44 to track motion, for example, of the pelvis in hip replacement surgery or the tibia and the femur in knee replacement surgery. As a result, the surgical system 10 is able to compensate for bone motion in real-time during surgery.

Identifying Release Locations

As mentioned above, the 3D model images created from scanned patient images or a database of bone models may be used to identify release locations, which are the points at which the soft tissue must be released in order to gain appropriate access to the femur for direct anterior total hip replacement, or similarly, as necessary for knee and shoulder applications. Several methods of using scanned image data, from CT scan, MRI, or the like, and combinations thereof, for building the three dimensional images which allow for identification of the release locations are described herein. While each of these methods are discussed in reference to the direct anterior total hip replacement, it should be appreciated that these methods, or comparable methods, of identifying soft tissue release may also be used in knee, shoulder and other surgical applications.

Figure 6:
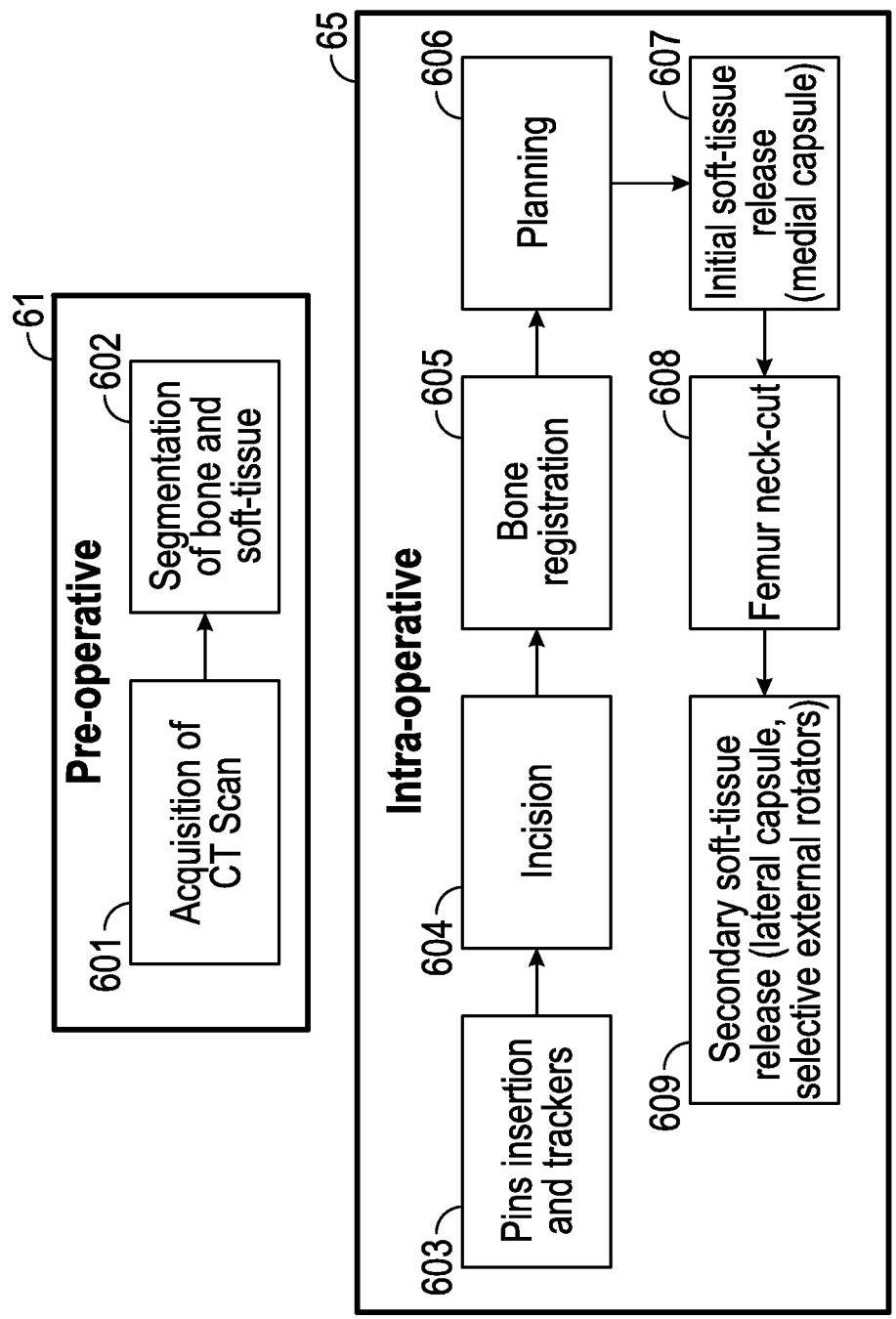
FIG. 6 is a flowchart of a process for identifying tissue release locations on a virtual bone model image and executing the tissue release, according to an exemplary embodiment.

Referring to FIG. 6, a first exemplary method is directed towards segmentation from a CT scan. The method includes acquiring a CT scan of the target area (step 601) and performing bone and soft tissue segmentation from the CT scan to generate a model image from which the locations of the soft tissue and the release locations can be determined (step 602). The steps of this method, including acquiring the scan and performing segmentation occur during a pre-operative stage 61. Once the three dimensional image is created, the intra-operative stage 65 follows which includes insertion of the bone pins P and anatomy trackers (step 603), making an incision (step 604), registering the anatomy of the patient (step 605), as discussed above, preparing the surgical plan (step 606), performing an initial soft tissue release (step 607), making a cut at the femur neck (step 608), and performing the secondary soft tissue releases as necessary to accommodate the arthroplasty procedure (step 609), as discussed in greater detail below. This exemplary method may further require the patient to be injected with a contrast agent to facilitate visualization of soft tissues on the CT scan.

Figure 7:
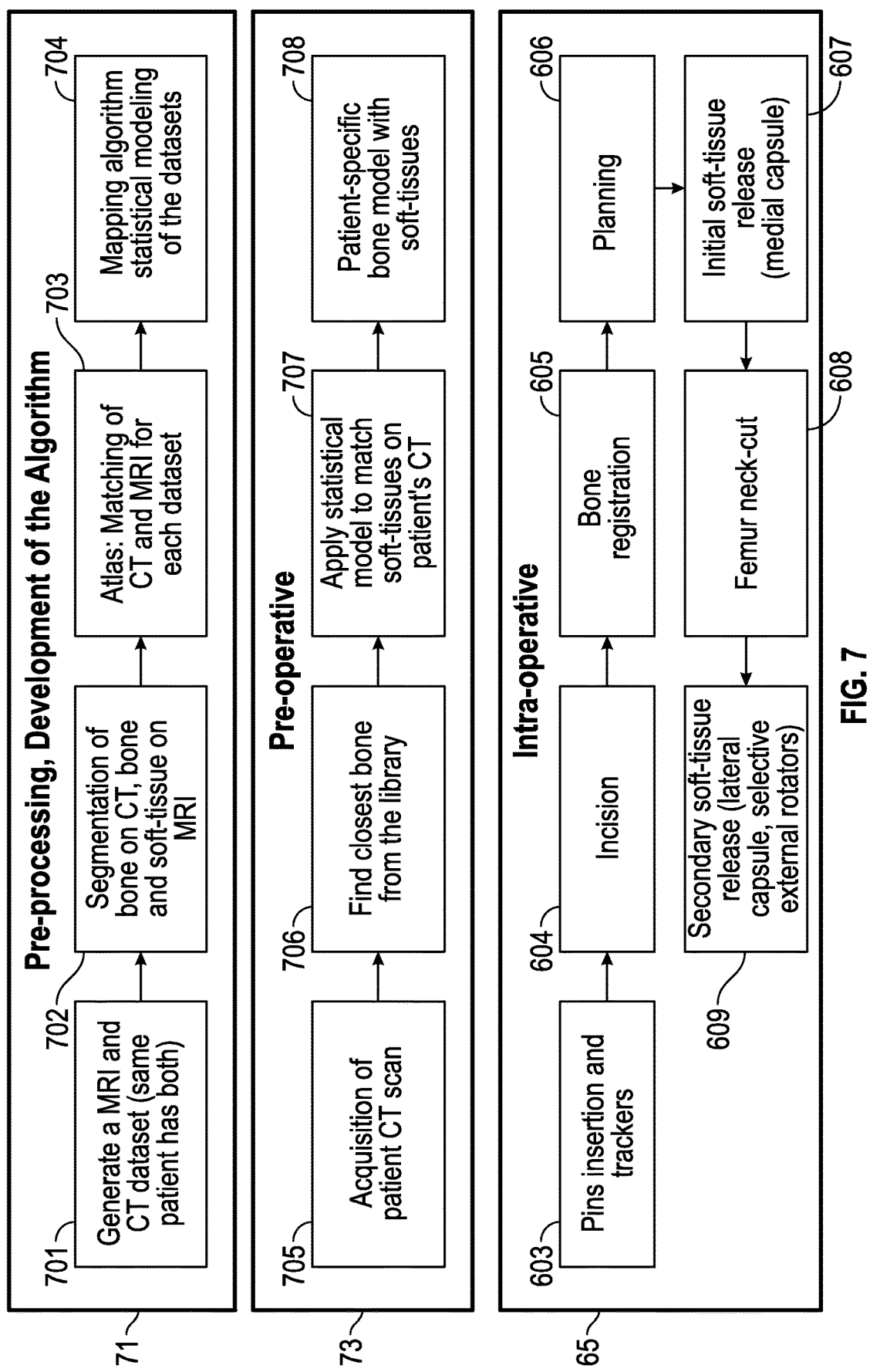
FIG. 7 is a flowchart of a process for identifying tissue release locations on a virtual bone model image and executing the tissue release, according to an exemplary embodiment.

As shown in FIG. 7, a second exemplary method is directed towards creating a patient-specific virtual model based on a CT scan and a statistical model. The method comprises a pre-processing stage 71 and a pre-operative stage 73, followed by the intra-operative stage 65 as described above. The pre-processing stage 71 involves generating MRI and CT datasets from a selected group of patients (step 701). Both the CT scans and MRI scans are segmented to develop a model (step 702). Then the MRI and CT scan of each dataset is matched, thereby creating an atlas of scans showing both the bone and the soft tissue (step 703), and a statistical model is created based on the variances found in the bone and the soft tissue among the datasets (step 704). Then, in a pre-operative stage 73, a patient's CT scan may be acquired (step 705) and the patient's bone is compared with the library of bones in the atlas (step 706). In an alternative embodiment, not illustrated, the surgeon may acquire points on the surface of a patient's bone intra-operatively by either touching the surface of the bone with a tracked probe or capturing points on surface of the bone with a non-contact probe (e.g. a tracked ultrasound device, a tracked laser device, etc) to create a point cloud representing the surface of the patients bone, which is then compared with the library of bones in the atlas (step 706). Based upon the patient's particular bone and the statistical model (step 707), the virtual image of the patient's bone and the soft tissue attachment points can be created (step 708). The intra-operative stage 65, as described above, follows.

Figure 8:
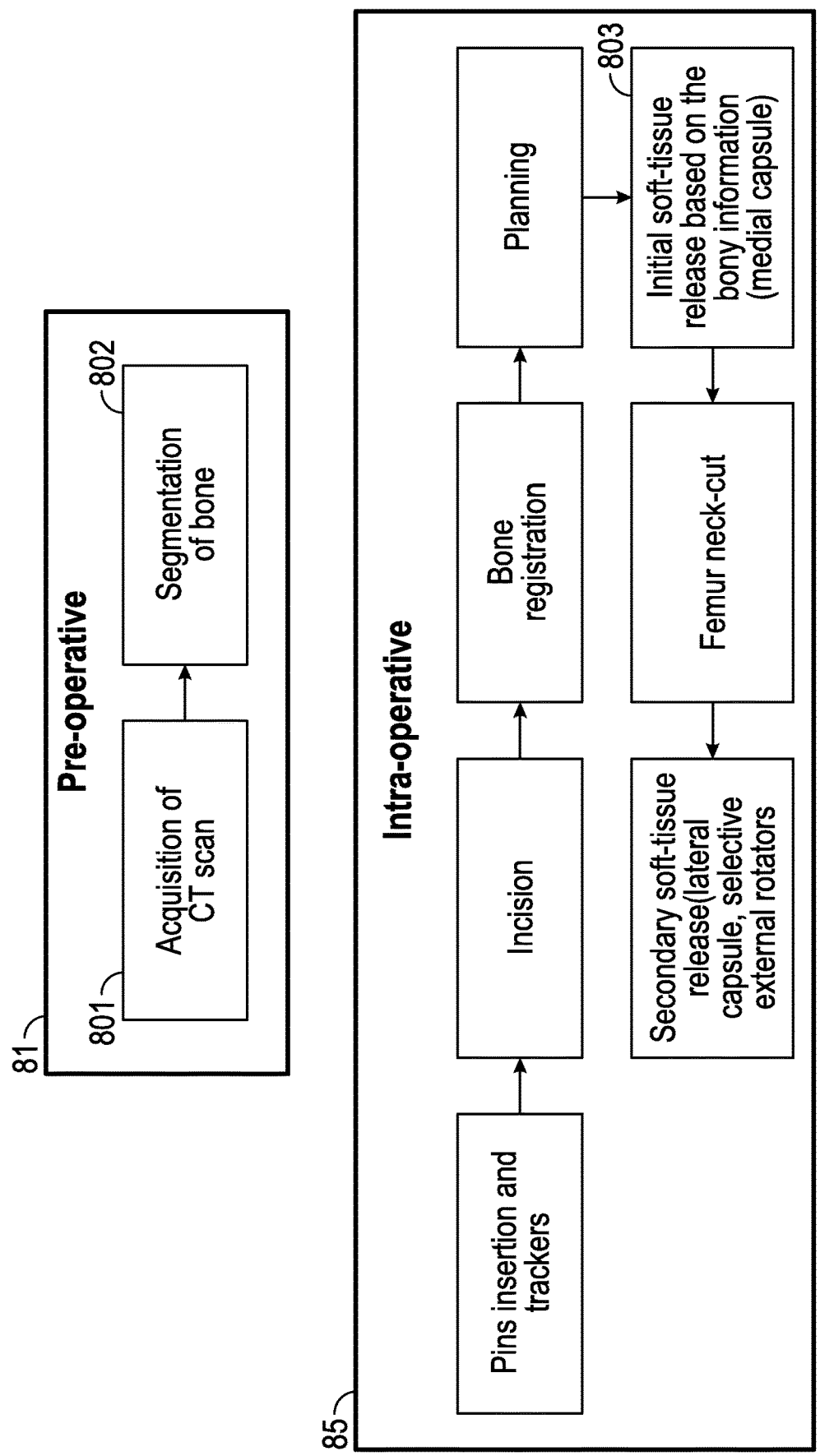
FIG. 8 is a flowchart of a process for identifying tissue release locations on a virtual bone model image and executing the tissue release, according to an exemplary embodiment.

As shown in FIG. 8, a third exemplary method is directed towards creating a virtual image based on CT scan showing bone alone. This method may require the surgeon to have common knowledge of the soft tissue surrounding the target bone, or may require application of certain algorithms or models to the pre-operative image data 50 to infer the location of soft tissue structures based on the overall structure of the bone and/or certain bony landmarks. In the pre-operative stage 81, a CT scan is acquired (step 801) and segmentation of the bone is performed to create a three dimensional representation of the anatomy (step 802). Based on this representation of the bone alone, the surgeon begins the intra-operative stage 85, which is similar to intra-operative stage 65, but that guidance provided to a surgeon for soft tissue release may be derived, either solely or primarily, from the structure of bone (step 803) without imaging the soft tissues.

A fourth exemplary method is directed towards any of the above mentioned methods of FIGS. 6-8 but that the patient data is based on an MRI rather than CT scan taken during the pre-operative stage 61, 73, 81. Once the data has been collected and the three dimensional representation of the patient anatomy has been created, the surgeon will begin the intra-operative stage 65.

Figure 9:
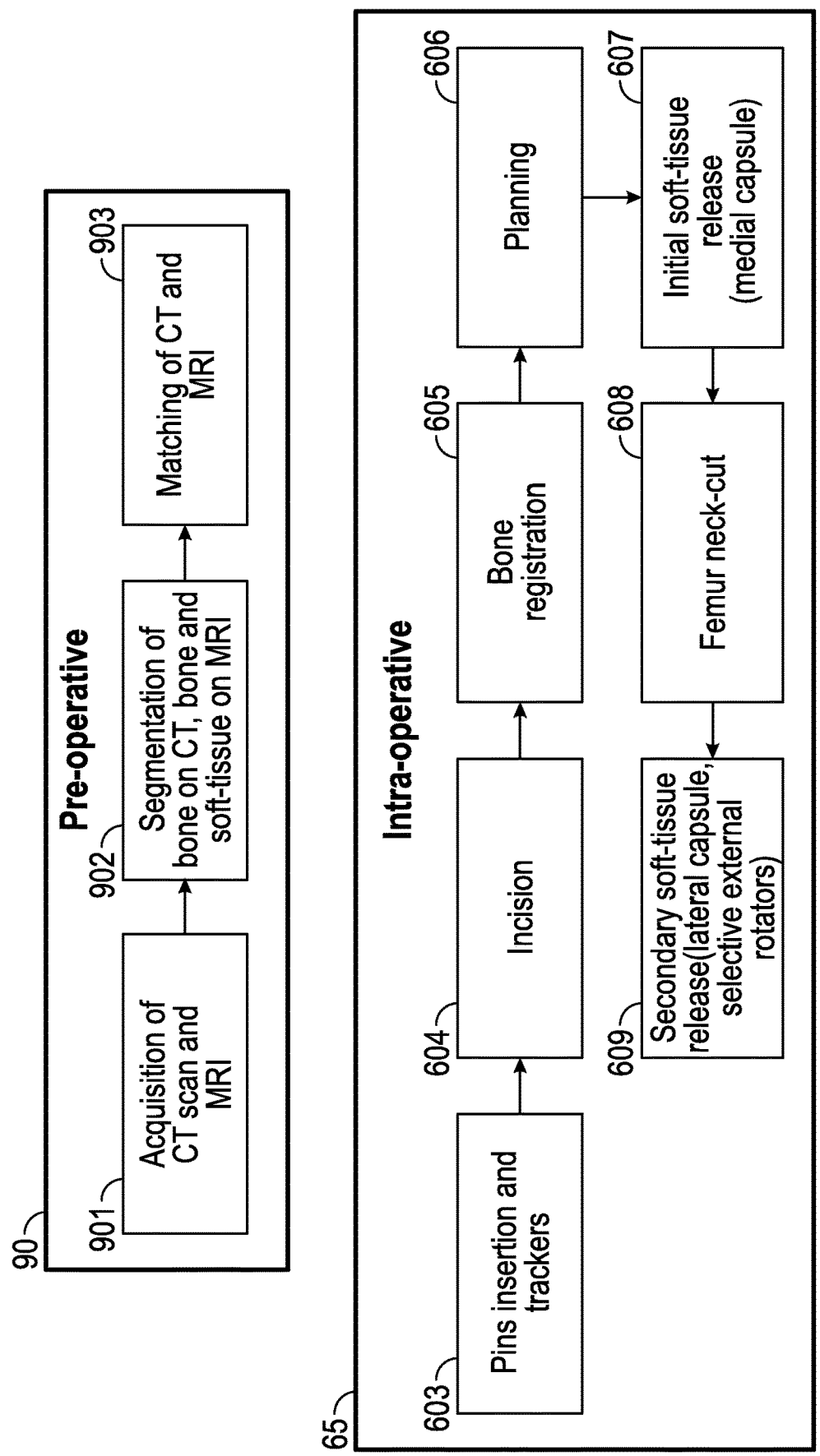
FIG. 9 is a flowchart of a process for identifying tissue release locations on a virtual bone model image and executing the tissue release, according to an exemplary embodiment.

As shown in FIG. 9, a fifth exemplary method is directed towards matching of CT and MRI data. This method includes a preoperative stage 90 that involves acquiring both a CT scan and MRI (step 901), segmenting the bone from the CT scan and the soft tissue from the MRI (step 902), and matching the two to create a very accurate three dimensional representation of the patient's anatomy (step 903). The same intra-operative procedure 65 is followed utilizing this representation.

Figure 10:
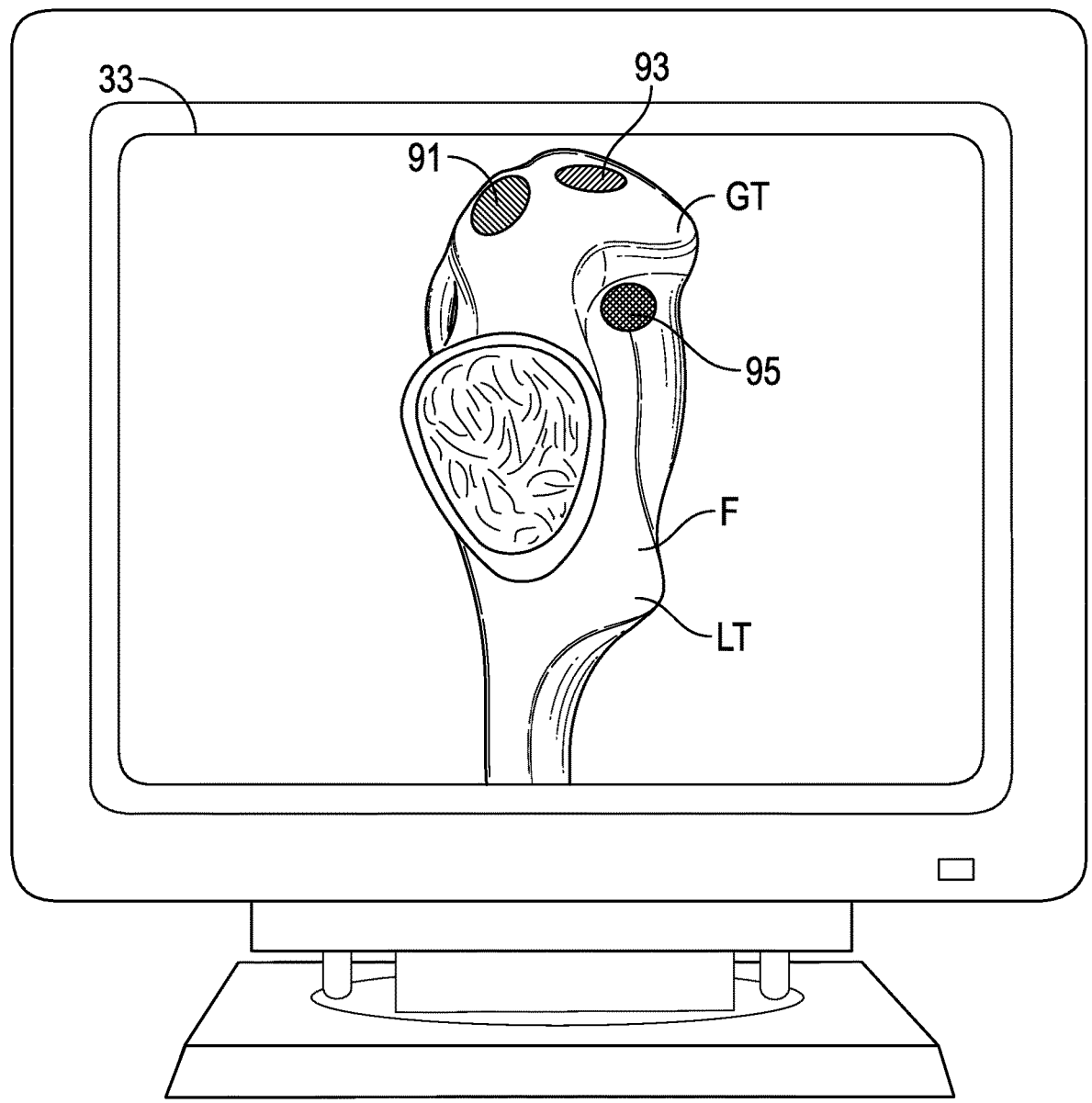
FIG. 10 is a plan view of a display screen according to an exemplary embodiment showing the soft tissue attachment points as shown on the display screen.
Figure 11:
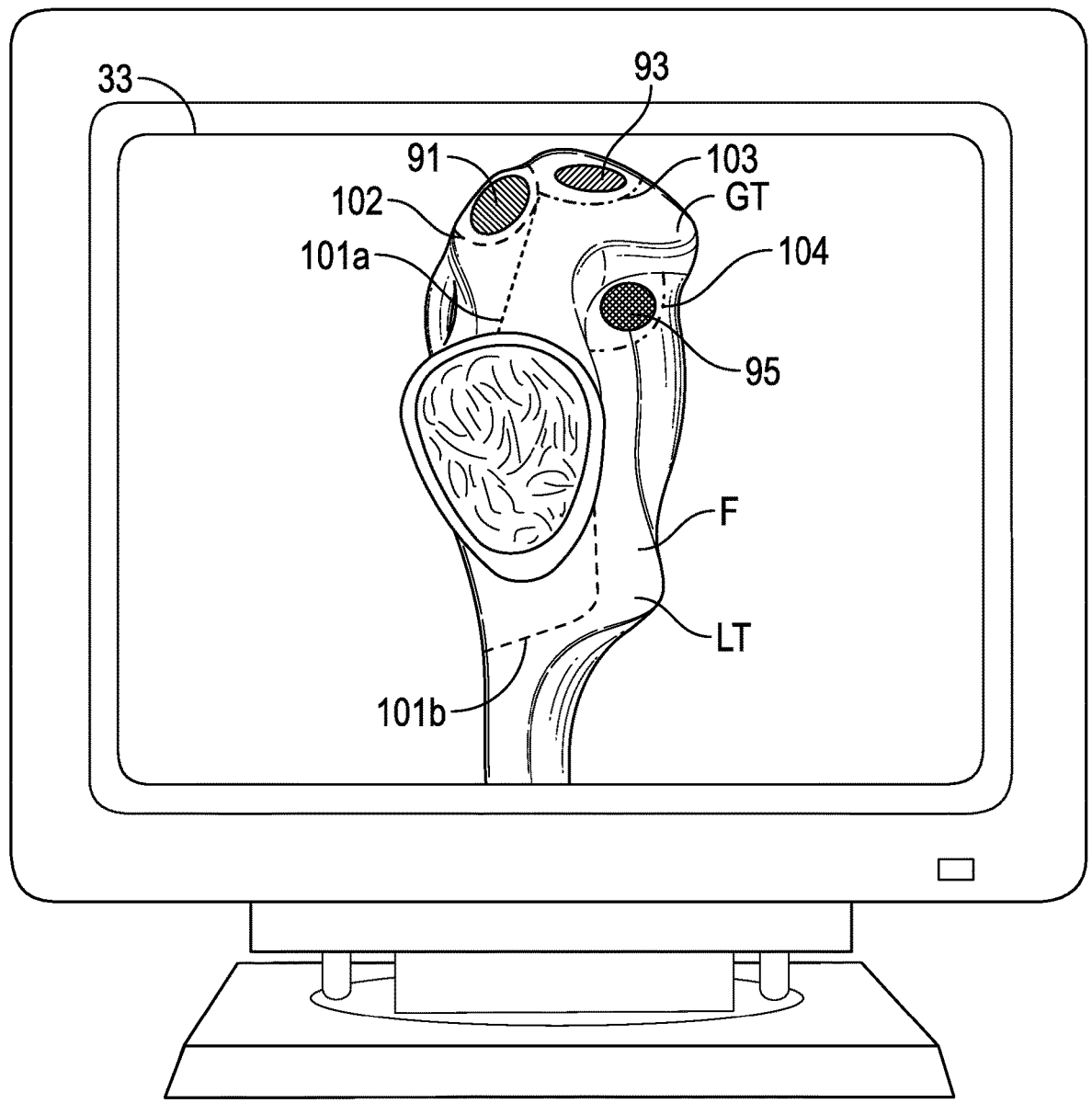
FIG. 11 is a plan view of a display screen according to an exemplary embodiment showing the soft tissue attachment points and proposed tissue release pathways as shown on the display screen.

As mentioned previously, optimal locations for release can be difficult to determine manually due to limited visibility of a patient's internal anatomy commonly encountered with direct anterior total hip replacement. Accordingly, in one embodiment, an identification of the soft tissue release locations is provided on the virtual image on the display device 33. As shown in FIG. 10, using a direct anterior total hip replacement as an example, the soft tissue attachment locations can be shown on the virtual image of the patient's femur by way of distinct attachment points 91, 93, 95. In a preferred embodiment, each of the attachment points 91, 93, 95 may be shown by way of unique indicia, such as each being displayed in a different color. For example, the area showing the attachment point of the conjoint tendon 91 may shown in a first color, the area showing the attachment point of the piriformis tendon 93 may be shown in a different color, and the area showing the attachment point of the obturator externus 95 may be shown in a third color. As shown in FIG. 11, the proposed pathways of the soft tissue release may also be outlined on the three dimensional representation of the patient's anatomy and displayed on the display device 33.

Performing Soft Tissue Release

Figure 12:
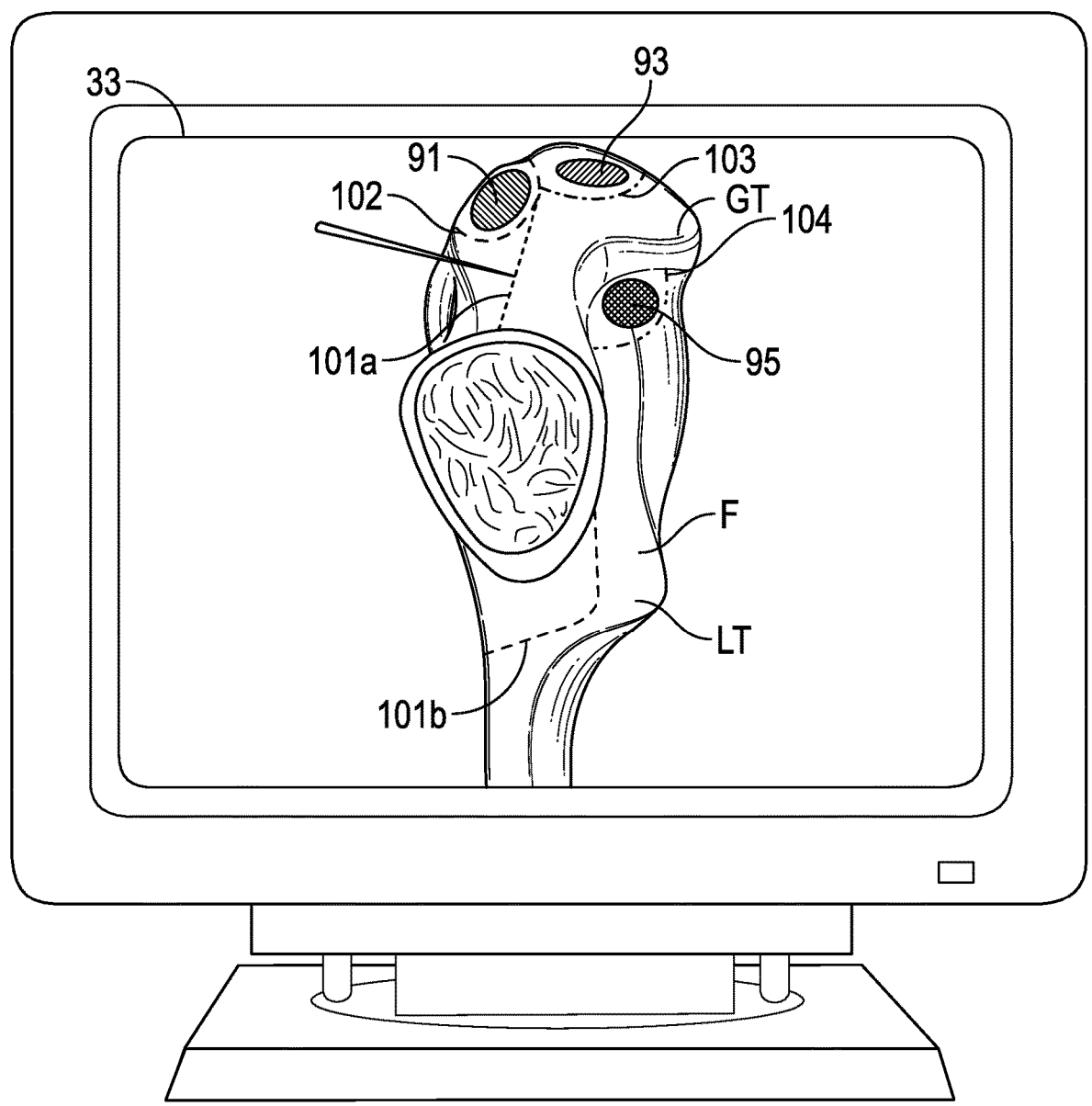
FIG. 12 is a plan view of a display screen according to an exemplary embodiment showing a virtual representation of the cutting instrument performing a soft tissue release as shown on the display screen.

Once the patient's specific anatomy has been registered with the tracking system 40, the release locations have been identified by one or more of the methods discussed above, and the release locations and release pathways have been depicted on the virtual image, the cutting device 20 can be applied to the area of the patient's proximal femur. The surgeon receives "real-time" visual feedback as to the location of the cutting device 20 by viewing the display device 33, such as the computer monitor, and verifying the location of the cutting tip 23 in relation to the 3D bone model, as shown in FIG. 12. The cutting device 20 can then be activated in the locations of optimal soft tissue release until optimal femoral exposure is achieved. The surgeon would manually activate the cutting device as with standard electrocautery (or similar instruments), such as by way of activation button 26.

Figure 13:
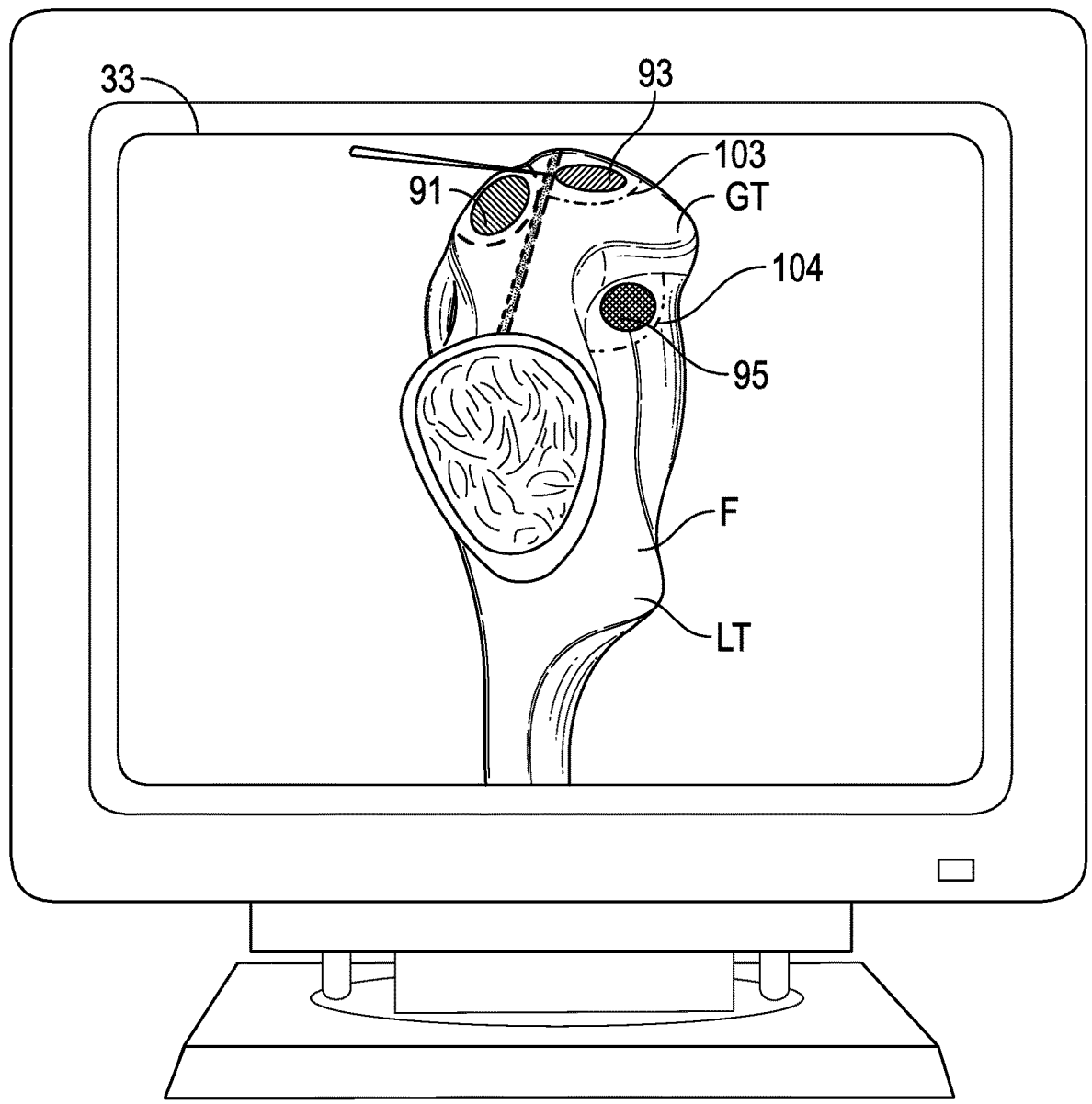
FIG. 13 is a plan view of a display screen according to an exemplary embodiment showing a virtual representation of the cutting instrument performing a soft tissue release as shown on the display screen.

As shown on the FIGS. 11-13, the proposed pathways for tissue release may be shown on the three dimensional representation of the patient's anatomy shown on the display device 33. The immediately upcoming tissue release pathway may be indicated to the surgeon, such as by showing the pathway in a defined color, emboldening the pathway, or showing the pathway in a flashing or pulsing manner. Each of the pathways may be shown in a different color to distinguish each of the desired pathways The embodiment shown displays a common set of pathways for soft tissue release used in direct anterior total hip replacement. For example, a first release pathway 101b will release the medial capsule to the level of the lesser trochanter LT and pathway 101a will release lateral capsule from the inner greater trochanter GT to the level of the piriformis. The surgeon then assesses for adequate femoral mobililty. If additional releases are necessary, the surgeon will move on to the next tissue release. For example, release pathway 102 will release the conjoint tendon from its attachment point 91. Again, femoral mobility is assessed and additional releases may be performed. Next, the surgeon may release the piriformis tendon from its attachment point 93, following release pathway 103. If proper mobility and femur broaching is still not achieved, the release pathway 104 may be followed to release the obturator externus tendon from its attachment point 95. Releases can be extended as needed until appropriated exposure is achieved. Tissue release procedures for direct anterior total hip replacement are known in the art and were, for example, detailed and described in Rodriguez J A, Walters B L, Cooper H J. Cadaveric Study: Introduction and Overview. Poster presented at: American Academy of Orthopaedic Surgeons Annual Meeting; 19-23 Mar. 2013; Chicago, Ill.

The soft tissue release may be further guided by an indication of the progression of the releases, as shown in FIG. 13. As the surgeon contacts bone with the cutting device 20, the bone model may turn a different color, or otherwise change in appearance, in the specific location contacted. The surgeon therefore receives "real time" feedback as to the progression of the release. The solid black line in FIG. 13 represents the pathway where the surgeon has activated the instrument on the bone surface and the soft tissue has thereby been released. In FIG. 13, the surgeon has released the lateral capsule and conjoint tendon.

Similar visual indicators of soft tissue attachment points and proposed release pathways can be shown for knee and shoulder applications on a virtual bone model of the patient's knee or shoulder. For example, in knee applications such as ligament balancing, a visual representation of the patient specific bone anatomy of the medial knee may be shown with mapped insertion points of the key medial soft tissue structures and proposed release pathways. Proposed soft tissue releases and the order of release for knee procedures have been described in publications such as Mullaji, A., Sharma, A., Marawar, S., & Kanna, R., Quantification of Effect of Sequential Posteromedial Release on Flexion and Extension Gaps. *The Journal of Arthroplasty*, 24(5), 795-805 and Koh, H. S. & In, Y., Semimembranosus Release as the Second Step of Soft Tissue Balancing in Varus Total Knee Arthroplasty. *The Journal of Arthroplasty*, 28(2),273-278 herein incorporated by reference in their entireties.

In addition to the visual, real-time feedback which the surgeon may use to guide the soft tissue releases, the surgical controller 31 may also be configured to cease operation, such as by cutting power to the cutting device 20, when the tracking system 40 determines that the cutting tip 23 of the cutting device 20 has moved outside the parameters of the proposed tissue release pathways. In one embodiment, the surgical controller 31 may be configured to cease operation, such as by cutting power to the cutting device 20, when the tracking system 40 determines that the cutting tip 23 has moved outside the parameters of the proposed tissue release pathways by a predetermined distance (e.g. 2 mm). In this way, even if the surgeon is manually activating the cutting device 20, by way of activation button 26 for example, the cutting instrument would still not function to cut tissue when it is outside the area as determined during the release location identification processes. Similarly, this soft tissue cutting guidance may include a system designed with haptic feedback capabilities, such as the haptic system and robotic arm as described in U.S. Pat. No. 8,010,180. In this way, the cutting device 20 would be attached to the robotic arm and its position determined by the tracking elements 22 and/or the positioning functionality of the robotic arm as described in the U.S. Pat. No. 8,010,180, and its movement could be controlled within the specified soft tissue cutting pathways, based upon the image data and the soft tissue release identification methods as discussed above.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, some elements shown as integrally formed may be constructed from multiple parts or elements, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present application contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an embodiment of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Although the figures may show or the description may provide a specific order of method steps, the order of the steps may differ from what is depicted. Also two or more steps may be performed concurrently or with partial concurrence. Such variation will depend on various factors, including software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. It should be understood that the present application is not limited to the details or methodology set forth in the description or illustrated in the figures. It should also be understood that the terminology is for the purpose of description only and should not be regarded as limiting.

The invention claimed is:

1. A surgical apparatus, comprising:
   a surgical device configured to be manipulated by a user to perform a soft tissue cutting procedure on a patient; and
   a surgical controller comprising a processing circuit configured to:
   create a virtual object comprising a three-dimensional model representing an anatomy of the patient;
   identify a plurality of soft tissue attachment points on the three-dimensional model;
   identify a proposed soft tissue release pathway relative to the virtual object and the plurality of soft tissue attachment points such that following the proposed soft tissue release pathway with the surgical device results in release of soft tissue from one or more of the soft tissue attachment points;
   determine a location of the surgical device in relation to the anatomy of the patient; and
   control a display device to provide real-time visualization of the location of the surgical device in relation to the proposed soft tissue release pathway based on the location of the surgical device in relation to the anatomy of the patient.

2. The surgical apparatus of claim 1, wherein the virtual object is created based upon data acquired during a pre-operative scan.

3. The surgical apparatus of claim 1, wherein the virtual object is created by acquiring locations of points on a surface of a bone of the patient to create a point cloud that represents the patient's anatomy.

4. The surgical apparatus of claim 1, wherein the processing circuit is configured to control the display device to display a plurality of unique indicia indicating locations of the plurality of soft tissue attachment points on the virtual object.

5. The surgical apparatus of claim 1, wherein the processing circuit is configured to control the display device to show an immediately upcoming tissue release pathway and one or more subsequent tissue release pathways, the immediately upcoming tissue release pathway visually distinguished from the one or more subsequent tissue release pathways.

6. The surgical apparatus of claim 1, wherein the processing circuit is configured to identify tissue release pathways that have been traversed by the surgical device and control the display device to indicate the tissue release pathways that have been traversed by the surgical device.

7. The surgical apparatus of claim 1, further comprising a tracking system having a detection device for determining the location of a tracked object and a trackable element on the tracked object, detectable by the detection device.

8. The surgical apparatus of claim 7, wherein the trackable element is configured to be attached to the surgical device.

9. The surgical apparatus of claim 7, wherein the trackable element is configured to be attached to an anatomy tracker that is attached to the anatomy of the patient.

10. The surgical apparatus of claim 7, wherein the trackable element comprises a reflective sphere.

11. The surgical apparatus of claim 1, wherein the surgical device comprises a cutting tip.

12. The surgical apparatus of claim 11, wherein the cutting tip comprises at least one of a scalpel blade, an electrocautery device, an ultrasonic cutting tool, or a vibratory cutting device adapted and configured to provide hemostasis.

13. The surgical apparatus of claim 1, wherein the processing circuit is further configured to adjust the virtual object in response to movement of the anatomy during a procedure by monitoring detected movement of the anatomy and then adjusting the virtual object in response to the detected movement.

14. The surgical apparatus of claim 1, further comprising the display device.

15. The surgical apparatus of claim 1, wherein the surgical controller is further programmed to cease operation of the surgical device when the surgical device is moved outside a predefined cutting region.

16. The surgical apparatus of claim 15, wherein the predefined cutting region is defined by a predetermined distance from the proposed soft tissue release pathway.

17. The surgical apparatus of claim 1, wherein:
the surgical device comprises a feedback mechanism configured to supply feedback to the user manipulating the surgical device; and
the processing circuit is configured to control the feedback mechanism to provide haptic guidance to the user based on the location of the surgical device in relsation to the anatomy of the patient.

18. A surgical apparatus, comprising:
a surgical device configured to be manipulated by a user to perform a soft tissue cutting procedure on a patient; and
a surgical controller comprising a processing circuit configured to:
create a virtual object representing an anatomy of the patient;
define a soft tissue release pathway such that following the proposed soft tissue release pathway with the surgical device releases soft tissue from the anatomy of the patient;
cause a display device to display the proposed soft tissue release pathway relative to the virtual object;
determine a location of the surgical device in relation to the anatomy of the patient; and
provide, via the display device, real-time visualization of the location of the surgical device in relation to the proposed soft tissue release pathway based on the location of the surgical device in relation to the anatomy of the patient.

19. The surgical apparatus of claim 18, wherein the surgical controller is further configured to identify a plurality of soft tissue attachment points on the virtual object which correspond to a plurality of soft tissue attachment points on the anatomy of the patient and provide, via the display device, a visualization of the plurality of soft tissue attachment points on the virtual object.

20. The surgical apparatus of claim 18, further comprising a tracking system having a detection device for determining the location of a tracked object and a trackable element on the tracked object, detectable by the detection device.

21. The surgical apparatus of claim 20, wherein the trackable element is configured to be attached to an anatomy tracker that is attached to the anatomy of the patient.

22. The surgical apparatus of claim 18, wherein the surgical device comprises a cutting tip.

23. The surgical apparatus of claim 22, wherein the cutting tip comprises at least one of a scalpel blade, an electrocautery device, an ultrasonic cutting tool, or a vibratory cutting device adapted and configured to provide hemostasis.

24. The surgical apparatus of claim 18, wherein the surgical controller is further configured to cease operation of the surgical device when the surgical device is moved outside a predefined cutting region.

25. The surgical apparatus of claim 24, wherein the predefined cutting region is defined by a predetermined distance from the proposed soft tissue release pathway.

26. The surgical apparatus of claim 18, wherein the processing circuit is configured to identify a tissue release pathway that has been traversed by the surgical device and control the display device to show the tissue release pathway that has been traversed by the surgical device.

27. The surgical apparatus of claim 1, wherein the surgical controller is further configured to control the display device to represent the soft tissue attachment points on the virtual model by indicia representative of the soft tissue attachment points, and wherein the indicia comprise markings on the virtual object indicating the location of the soft tissue attachment points.

28. The surgical apparatus of claim 1, wherein the processing circuit is configured to control the display device to represent a plurality of soft tissue attachment points on the virtual model by indicia representative of the soft tissue attachment points, and wherein the indicia comprise colored markings on the virtual object indicating the location of the soft tissue attachment points.

29. The surgical apparatus of claim 28, wherein the indicia representative of the soft tissue attachment points comprise a first colored marking indicating the location of a first soft tissue attachment point and a second colored marking indicating the location of a second soft tissue attachment point, wherein the first colored marking is a different color than the second colored marking.

30. The surgical apparatus of claim 18, wherein the processing circuit is further configured to provide, via the display device, a visualization of indicia representative of soft tissue attachment points to be released, wherein the indicia comprise markings on the virtual object indicating the location of the soft tissue attachment points.

31. The surgical apparatus of claim 30, wherein the markings are colored.

32. The surgical apparatus of claim 31, wherein the indicia representative of the soft tissue attachment points to be released comprise a first colored marking indicating the location of a first soft tissue attachment point and a second colored marking indicating the location of a second soft tissue attachment point, the first colored marking having a different color than the second colored marking.

* * * * *